United States Patent [19]

Orsolini et al.

[11] Patent Number: 5,637,568
[45] Date of Patent: Jun. 10, 1997

[54] COMPOSITION FOR THE SUSTAINED AND CONTROLLED RELEASE OF MEDICAMENTOUS SUBSTANCES AND A PROCESS FOR PREPARING THE SAME

[75] Inventors: Piero Orsolini; Frédéric Heimgartner, both of Martigny, Switzerland

[73] Assignee: Asta Medica Ag, Frankfurt am Main, Germany

[21] Appl. No.: 210,097

[22] Filed: Mar. 16, 1994

Related U.S. Application Data

[63] Continuation of Ser. No. 915,490, Jul. 16, 1992, abandoned.

[30] Foreign Application Priority Data

Jul. 22, 1991 [CH] Switzerland ............... 02178/91

[51] Int. Cl.⁶ ............................................. A61K 38/00
[52] U.S. Cl. ..................... 514/15; 530/328; 424/489; 424/490; 424/491
[58] Field of Search ..................... 514/15; 530/328; 424/489, 490–491

[56] References Cited

U.S. PATENT DOCUMENTS

| | | | |
|---|---|---|---|
| 3,737,337 | 6/1973 | Schnoring et al. | 117/100 |
| 3,891,570 | 6/1975 | Fukushima et al. | 252/316 |
| 3,976,071 | 8/1976 | Sadek | 424/22 |
| 4,341,767 | 7/1982 | Nestor et al. | 424/177 |
| 4,384,975 | 5/1983 | Fong | 427/213.36 |
| 4,389,330 | 6/1983 | Tice et al. | 427/213.36 |
| 4,652,441 | 3/1987 | Okada et al. | 424/19 |
| 4,835,139 | 5/1989 | Tice et al. | 514/16 |
| 4,954,298 | 9/1990 | Yamamoto | 264/4.6 |
| 5,134,122 | 7/1992 | Orsolini | 514/15 |
| 5,187,150 | 2/1993 | Speiser et al. | 514/2 |
| 5,192,741 | 3/1993 | Orsolini et al. | 514/4 |
| 5,445,832 | 8/1995 | Orsolini et al. | 424/491 |

FOREIGN PATENT DOCUMENTS

| | | |
|---|---|---|
| 0058481 | 8/1982 | European Pat. Off. . |
| 0052510 | 8/1986 | European Pat. Off. . |
| 0058481 | 10/1986 | European Pat. Off. . |
| 0292710 | 5/1988 | European Pat. Off. . |
| 2491351 | 9/1981 | France . |
| 2620621 | 9/1988 | France . |
| 2649319 | 7/1990 | France . |
| 4023134A1 | 7/1989 | Germany . |
| 2211091 | 10/1988 | United Kingdom . |
| 2234896 | 2/1991 | United Kingdom . |
| WO90/13361 | 11/1990 | WIPO . |

OTHER PUBLICATIONS

Bajusz, et al, "New Antagonists of LHRH", Int. J. Peptide Protein Res. 32, 1988, 425–435.

*Primary Examiner*—Cecilia J. Tsang
*Assistant Examiner*—S. G. Marshall
*Attorney, Agent, or Firm*—Pennie & Edmonds

[57] ABSTRACT

A composition designed for the sustained and controlled release of medicamentous peptide substances having the formula (I):

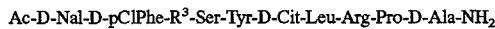

Ac-D-Nal-D-pClPhe-$R^3$-Ser-Tyr-D-Cit-Leu-Arg-Pro-D-Ala-$NH_2$ wherein $R^3$ is D-Pal or D-Trp. The composition is obtained in the form of microspheres of a biodegradable polymeric material incorporating a water-insoluble salt of the peptide of formula (I).

14 Claims, No Drawings

COMPOSITION FOR THE SUSTAINED AND CONTROLLED RELEASE OF MEDICAMENTOUS SUBSTANCES AND A PROCESS FOR PREPARING THE SAME

This is a continuation of application Ser. No. 07/915,490, filed Jul. 16, 1992, now abandoned.

FIELD OF THE INVENTION

A composition designed for the sustained and controlled release of medicamentous peptide substances, obtained in the form of microspheres of a biodegradable polymeric material incorporating said medicamentous substance. A process for its preparation.

SUMMARY OF THE INVENTION

A composition designed for the sustained and controlled release of a medicamentous peptide substance, having the formula (I)

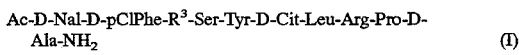

wherein $R^3$ is D-Pal or D-Trp, in the form of microspheres of a biodegradable polymeric material including a water-insoluble salt of the peptide of formula (I).

A process for the preparation of the above composition which consists firstly in converting a water-soluble peptide salt into a water-insoluble peptide salt, then suspending said peptide salt in a solution of a biodegradable polymeric material, converting said suspension into an oil-in-water type emulsion, and finally isolating the microspheres of biodegradable polymer after transfer of the oil-in-water emulsion into an excess of an aqueous medium.

STATE OF THE ART

Various solutions have been proposed to this day for the preparation of compositions capable of a sustained and a controlled release of medicamentous substances, making use of the manufacture of biodegradable implants, of microencapsulation or of the preparation of biodegradable porous matrices obtained for example as microspheres or microparticles of various dimensions. In this respect, one can mention EP-A-0052510 for microencapsulation by phase separation of water-soluble drugs and EP-A-0058481 or U.S. Pat. No. 3,976,071 for the preparation of implants or of biodegradable porous matrices, based mainly on polylactide or on copolylactide-glycolide. These techniques make use of a prior dissolution in an organic solvent of the biodegradable polymer or copolymer used as support and, if required, the dissolution of the medicamentous substance itself.

Other techniques, also capable of yielding microcapsules or microspheres, make use of emulsification procedures, the most important step of such procedures being the obtention of an oil-in-water type emulsion from an organic solution of polymeric material and an aqueous solution of the peptide— see in this respect U.S. Pat. Nos. 4,384,975, 3,891,570, 4,389,330, 3,737,337, 4,652,441 or WO-90/13361. In any case however, those versed in the art are obliged to develop techniques which are complex and difficult to control, in order to reduce as much as possible the losses of the highly water-soluble active peptide substances, such as for example a double emulsification.

THE INVENTION

In a process using the formation of an emulsion of the oil-in-water type followed by its transfer into an aqueous medium, the invention enables, against all expectations, to overcome advantageously the short-commings of techniques known to this day.

Actually, by firstly proceeding to the conversion of a water-soluble peptide salt of formula (I) into a water-insoluble peptide salt, the invention makes available to those versed in the art, quite a novel means of taking advantage of the relative solubilities of the ingredients which are used and in particular of the solvents and "non-solvents" involved.

PREFERRED EMBODIMENTS OF THE INVENTION

Peptides having the formula (I) are defined as LHRH analogues; they can be used advantageously in the therapeutic treatment of hormone-dependent troubles. Unless specified otherwise, the amino acids defining formula (I) have the L configuration. D-Nal stands for D-3-(2-naphtyl)-alanine and D-Pal stands for D-3-(3-pyridyl)alanine.

The composition according to the invention is in the form of microspheres of a biodegradable polymeric material including a water-insoluble salt of the peptide of formula (I). The composition is used in a pharmaceutical preparation for parenteral administration. This composition, including e. g. 5% in weight of the water-insoluble salt, can achieve the sustained release of said peptide over several days after parenteral administration to man or animal.

The invention also refers to a process for the preparation of the composition defined hereabove.

More particularly, one of the objects of the invention is a process which is characterized by the fact that:

a. a water-soluble peptide salt of formula (I) is converted into a water-insoluble peptide salt;

b. said water-insoluble peptide salt is suspended in an organic medium containing the bio-degradable polymeric material in the dissolved state;

c. said organic suspension is dispersed in an aqueous medium forming the continuous phase of the resulting emulsion;

d. said emulsion is transferred into an excess of an aqueous medium, and finally the microspheres thus obtained are separated from the liquid phase.

The first phase of the process consists in converting, by means of conventional techniques, a water-soluble peptide salt into a water-insoluble peptide salt. By "water-soluble" is meant a peptide salt having a water solubility in excess or equal to 0.1 mg/ml at 25° C., preferably in excess or equal to 1.0 mg/ml.

By "water-insoluble" is meant a peptide salt having a water solubility lesser or equal to 0.1 mg/ml at 25° C. Peptide salts such as pamoate, tannate, stearate or palmitate satisfy this definition.

As to the biodegradable polymeric material, the most commonly used are polymers such as a polylactide, a polyglycolide or a copolymer of lactic and glycolic acids.

Amongst the preferred polymeric materials, one should mention the copolymers of lactic and glycolic acids (PLGA) and in particular the copolymers of L- or D,L-lactic acid containing from 45 to 90% (molar) of lactic acid units and respectively 55 to 10% (molar) of glycolic acid units.

As to the solvent selected for the polymeric material, one can use an organic solvent such as for example methylene chloride, but in any case, the solvent must be a "non solvent" for the selected peptide or peptide salt.

According to the invention, once said peptide or salt is suspended in the organic solution of the polymeric material, this solution is incorporated into a predetermined amount of an aqueous medium, most generally of water complemented with an appropriate surfactant. The objective is to form rapidly a homogeneous emulsion of the oil-in-water type, said aqueous medium functioning to provide the continuous phase. Various factors are to be considered when preparing such an emulsion, which in turn influence the size or the structure of the microspheres resulting from the process. One of the factors which must be taken into consideration is the rate of addition of the organic solution to the aqueous medium; another one can be the temperature or further the agitation speed or the energy of dispersion (ultrasonic treatment), with the last mentioned parameter influencing in particular the size of the final microspheres. It is within the capacity of those versed in the art to select the methods and the conditions of emulsification suitable for achieving the intended purpose.

In the preparation of said emulsion, it may also prove advantageous to modify the volume ratio of the phases in contact, in particular to decrease the initial volume of the organic phase with respect to that of the aqueous phase. In some cases, owing to the volatility of the organic solvents which are used—for example methylene chloride—the evaporation occurring spontaneously during agitation may already prove sufficient; in other cases, this desirable phenomenon may be accelerated by proceeding to a partial evaporation, under reduced pressure.

Once the organic-aqueous emulsion has been stabilized, it is transferred into an excess amount of an aqueous medium, most generally water. The purpose of this operation is to intensify the hardening of the embryonic microspheres formed in the emulsion, by extracting the organic solvent still remaining inside said microspheres. This operation is also aimed at eliminating at the same time trace amounts of surfactant which may have remained in the body of the polymer during its final hardening phase. It is to be noted, that water is a "non-solvent" for both the biodegradable polymeric material such as PLGA for example and for the peptide salt trapped inside said microspheres. This situation is particularly favourable for the indispensable extraction of the residual polymer solvent, such as for example $CH_2Cl_2$.

Having transferred said emulsion into an excess of an aqueous medium, the hardened microspheres are collected using conventional techniques, for example by centrifugation, filtration or by gravity settling. The same applies to the washing, purification and drying operations.

One of the advantages of the process of the invention is that it makes it possible to obtain microspheres the size of which can be accurately controlled, this control taking place mainly during the preparation of the emulsion (agitation speed for example). Another advantage is that a particularly high peptide loading can be achieved, amounting to 5, 10 or 20% in weight, or even higher, depending on conditions. Further, the yield of the peptide or peptide salt incorporation is particularly high; this is due mainly to the prior conversion of the selected peptide from a water-soluble salt into a water-insoluble salt.

The microspheres obtained according to the process of the invention from the above-mentioned ingredients are then used after being appropriately sterilized, for the preparation of suspensions used in parenteral administration, for example by intramuscular or subcutaneous injection.

The invention is illustrated by the following examples. The operational conditions used in these examples do not limit the invention in any way.

EXAMPLE 1

3 g of the acetate of the LHRH analogue of the formula:

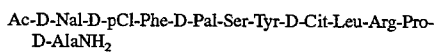
Ac-D-Nal-D-pCl-Phe-D-Pal-Ser-Tyr-D-Cit-Leu-Arg-Pro-D-AlaNH$_2$ were converted into the corresponding pamoate by conventional techniques and treated in such a manner as to obtain particles having an average size of approximately 10 microns.

0.317 g of said pamoate were then suspended in 20 ml of $CH_2Cl_2$, and said suspension was added to 20 ml of $CH_2Cl_2$ containing 1.683 g of dissolved copolymer of D,L-lactic and glycolic acids (PLGA) 75:25 (molar %/inherent viscosity of 0.82 in HFIP). The mixture was prepared at room temperature, under stirring, to obtain a suspension which was perfectly homogeneous.

The resulting suspension was then poured, in one portion, into 500 ml of water containing 0.075% dissolved methoxycellulose and stirring of the mixture was continued for about 90 min. at room temperature (speed of agitation: 900 rpm). The evolution of the emulsion was monitored at regular intervals of time, on the average every 30 minutes, by taking a sample and examining the microspheres obtained with a microscope.

Once the stirring is ended (stabilization of the size reduction of the microspheres), said emulsion is transferred in one portion into 2 l of water maintained at approximately 10° C., while stirring the mixture until homogenization.

The microspheres of PLGA were isolated from the reaction mixture and purified by successive centrifugations alternating with washings with $H_2O$, and finally filtered and dried under reduced pressure. 1.61 g of PLGA microspheres were thus collected (yield : 80%), which included more than 94% particles having a diameter lesser than 100 microns (maximum at 55–85 microns).

The analysis (dissolution of the solid PLGA, extraction and determination of the peptide by HPLC) shows that the loading of the pamoate of the microspheres amounts to 9.05% in weight (theoretical: 10%).

The microspheres thus obtained were subsequently subjected to a sterilization by gamma rays and suspended in an appropriate sterile vehicle. In vivo tests (determination of the blood testosterone level in male rats) confirmed the regular release of the active substance.

EXAMPLE 2

Exactly the same procedure was used as in Example 1, with 0.634 g of the pamoate of the LHRH analogue, for 1.366 g of PLGA 75:25.

PLGA microspheres: 1.70 g (yield: 85%).

Level of loading: 18.3% (theoretical: 20%)

The microspheres thus obtained were subsequently subjected to a gamma ray sterilization and suspended in an appropriate sterile vehicle. In vivo tests (determination of the blood serum level of the analogue in male rats) confirm the regular release of a biologically significative amount of active substance over at least 24 days.

| TIME (days) | DETERMINATION OF PEPTIDE (ng/ml) |
|---|---|
| 0 + 3 hours | 47.1 |
| 1 | 48.9 |
| 2 | 52.2 |
| 3 | 46.9 |
| 6 | 50.4 |
| 8 | 40.1 |
| 10 | 42.1 |
| 14 | 29.8 |
| 16 | 33.5 |
| 20 | 33.0 |
| 24 | 25.6 |

These results are further confirmed by analyses carried out on subjects sacrificed at D30: loss of weight of the testes of at least 80%, loss of weight of the seminal vesicles of at least 90%.

EXAMPLE 3

Exactly the same procedure was used as in example 1, but making use of the peptide of formula:

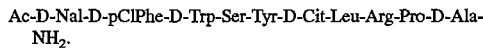
Ac-D-Nal-D-pClPhe-D-Trp-Ser-Tyr-D-Cit-Leu-Arg-Pro-D-Ala-NH₂.

By converting the acetate salt thereof into the corresponding pamoate and by subjecting the latter to the same subsequent treatment, similar results were achieved.

What we claim is:

1. A sustained and controlled release composition consisting essentially of microspheres of biodegradable polymeric material which incorporate therein a water-insoluble salt of a medicamentous peptide substance having the formula (I):

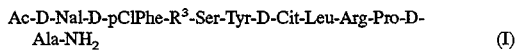
Ac-D-Nal-D-pClPhe-R³-Ser-Tyr-D-Cit-Leu-Arg-Pro-D-Ala-NH₂     (I)

wherein R³ is D-Pal or D-Trp.

2. Composition according to claim 1, wherein the water-insoluble peptide is a pamoate, tannate, stearate or palmitate.

3. Composition according to claim 1, wherein the biodegradable polymeric material is a polylactide, a polyglycolide or a copolymer of lactic and glycolic acids.

4. Composition according to claim 1, wherein the copolymer of lactic and glycolic acids is a copolymer of L- or D,L-lactic acid containing from 45 to 90% (molar) of lactic acid units and respectively 55 to 10% (molar) of glycolic acid units.

5. Composition according to one of claims 1 in the form of microspheres of a 75:25 (molar %) copolymer of lactic and glycolic acids, including at least 5% in weight of the pamoate salt of a peptide of formula (I).

6. A sustained and controlled release composition consisting essentially of micropheres of a biodegradable polymeric material which incorporate therein a water-insoluble salt of a medicamentous peptide substance having the formula (I):

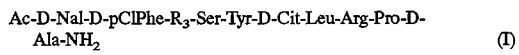
Ac-D-Nal-D-pClPhe-R₃-Ser-Tyr-D-Cit-Leu-Arg-Pro-D-Ala-NH₂     (I)

wherein R³ is D-Pal or D-Trp, said composition prepared by process comprising the steps of:

a) converting a water-soluble peptide salt of formula (I) into a water-insoluble peptide salt;

b) suspending said water-insoluble peptide salt in an organic medium containing the biodegradable polymeric material in the dissolved state to afford an organic suspension;

c) dispersing said organic suspension in an aqueous medium which forms the continuous phase of the resulting emulsion, said aqueous medium consisting essentially of water;

d) transferring said emulsion into an excess of an aqueous medium; and e) separating microspheres thus obtained from the liquid phase, said microspheres containing a pharmaceutically effective amount between about 5–20% by weight of said water-insoluble peptide salt.

7. Composition according to claim 1, wherein before the transfer of the oil-in-water emulsion into an excess of aqueous medium, a partial evaporation of the organic solvent forming the oil phase is carried out.

8. Composition according to claim 1, wherein the water-insoluble peptide salt is a pamoate, a tannate, a stearate or a palmitate.

9. Composition according to one of claim 1, wherein the biodegradable polymeric material is a polylactide, a polyglycolide, or a copolymer of lactic and glycolic acids.

10. Composition according to claim 1, wherein the copolymer of lactic and glycolic acids is a copolymer of L- or D,L-lactic acid containing from 45 to 90% (molar) of lactic acid units and respectively 55 to 10% (molar) of glycolic acid units.

11. Process according to claim 6, wherein the water-insoluble peptide salt is present in the microspheres in an amount of from about 5% by weight.

12. The composition of claim 6, wherein said aqueous medium additionally contains a surfactant.

13. A sustained and controlled release composition consisting essentially of microspheres of a biodegradable polymeric material which incorporate therein a water-insoluble salt of a medicamentous peptide substance, said water-insoluble salt having a water solubility less than or equal to 0.1 mg/ml at 25° C., said peptide substance having the formula (I):

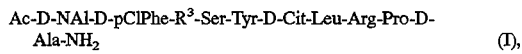
Ac-D-NAl-D-pClPhe-R³-Ser-Tyr-D-Cit-Leu-Arg-Pro-D-Ala-NH₂     (I), wherein R³ is D-Pal or D-Trp and said biodegradable polymeric material being a polylactide, a polyglycolide, or a copolymer of lactic and glycolic acids, said composition prepared by a process comprising the steps of:

a) converting a water-soluble peptide salt of formula (I) into a water-insoluble peptide salt;

b) suspending said water-insoluble peptide salt in an organic medium containing the biodegradable polymeric material in the dissolved state to afford an organic suspension;

c) dispersing said organic suspension in an aqueous medium which forms the continuous phase of the resulting emulsion, said aqueous medium consisting essentially of water and a surfactant;

d) transferring said emulsion into an excess of an aqueous medium; and e) separating microspheres thus obtained from the liquid phase, said microspheres containing a pharmaceutically effective amount between about 5–20% by weight of said water-insoluble peptide salt.

14. The composition of claim 13, wherein said copolymer of lactic and glycolic acids is a copolymer of L- or D,L-lactic acid containing from 45 to 90% (molar) of lactic acid units and respectively 55 to 10% (molar) of glycolic acid units.

* * * * *